US007351842B2

(12) United States Patent
Druzgala (10) Patent No.: US 7,351,842 B2
(45) Date of Patent: *Apr. 1, 2008

(54) COMPOUNDS FOR TREATMENT OF CARDIAC ARRHYTHMIA AND METHODS OF USE

(75) Inventor: Pascal Druzgala, Santa Rosa, CA (US)

(73) Assignee: ARYx Therapeutics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/423,559

(22) Filed: Jun. 12, 2006

(65) Prior Publication Data

US 2006/0276535 A1    Dec. 7, 2006

Related U.S. Application Data

(63) Continuation of application No. 11/101,995, filed on Apr. 8, 2005, now Pat. No. 7,105,568.

(60) Provisional application No. 60/560,917, filed on Apr. 9, 2004.

(51) Int. Cl.
*C07D 307/02* (2006.01)
*A61K 31/34* (2006.01)

(52) U.S. Cl. ............... 549/467; 549/468; 514/469
(58) Field of Classification Search ............... 549/467, 549/468; 514/469
See application file for complete search history.

(56) References Cited

U.S. PATENT DOCUMENTS

| 4,575,513 A | 3/1986 | Descamps et al. |
| 7,105,568 B2 * | 9/2006 | Druzgala ................ 514/469 |

FOREIGN PATENT DOCUMENTS

| WO | 01/29018 | 4/2001 |
| WO | 03/050102 | 6/2003 |

OTHER PUBLICATIONS

Abdollah, Hoshiar et al., "Antiarrhythmic Effects of Desethylamiodarone in Dogs with Subacute Myocardial Infarction and Inducible Ventricular Arrhythmias," Journal of Cardiovascular Pharmacology, 13(1), 37-44 Coden JCPCDT: ISSN: 0160-2446, 1989, XP008050098.

* cited by examiner

*Primary Examiner*—D. Margaret Seaman
(74) *Attorney, Agent, or Firm*—McDonnell Boehnen Hulbert & Berghoff LLP (57) ABSTRACT

The subject invention provides novel compounds for treatment of cardiac arrhythmia and methods of use.

42 Claims, 6 Drawing Sheets

COMPOUNDS FOR TREATMENT OF CARDIAC ARRHYTHMIA AND METHODS OF USE

CROSS-REFERENCE TO RELATED APPLICATIONS

This application is a continuation of U.S. application Ser. No. 11/101,995, filed Apr. 8, 2005 now U.S. Pat. No. 7,105,568 which claims the benefit of U.S. Provisional Application No. 60/560,917, filed Apr. 9, 2004.

BACKGROUND OF INVENTION

1. Field of the Invention

This invention relates to the field of treatment of cardiac arrhythmia and, in particular, new compounds and associated methods useful in such treatments, 2. Summary of Related Art Congestive heart failure (CHF) is a disease affecting approximately 2% of the population of the United States (Sami, M. H. [1991] J. Clin. Pharmacol. 31:1081). Despite advances in the diagnosis and treatment of CHF, the prognosis remains poor with a 5-year mortality rate higher than 50% from the time of diagnosis (McFate Smith, W. [1985] Am. J. Cardiol. 55:3A; McKee, P. A., W. P. Castelli, P. M. McNamara, W. B Kannel [1971] N. Engl. J. Med. 285: 1441). In patients with CHF, the rate of survival is lowest in those patents with severe depression of left ventricular function and patients who have frequent ventricular arrhythmias. Patients with ventricular arrhythmias and ischemic cardiomyopathy have an increased risk of sudden death. The presence of ventricular tachycardia in patients with severe CHF results in a three-told increase in sudden death compared to those without tachycardia (Bigger, J. T., Jr. [1987] Circulation 75 (Supplement IV):28). Because of the high prevalence of sudden unexpected death in patients with CHF, there has been a growing interest in the prognostic significance of arrhythmias in these patients.

Several compounds have been used in the management of cardiac arrhythmias in patients with congestive heart failure. Unfortunately, anti-arrhythmic drug therapy has been disappointing, The efficacy of anti-arrhythmic drugs markedly decreases as left ventricular function declines, such that only a small fraction of patients with CHF are responsive to anti-arrhythmic therapy. No anti-arrhythmic drug has prevented sudden death in patients with CHF. There is even a question of increased mortality associated with certain anti-arrhythmic drugs (the CAST investigators [1989] N. Engl. J. Med. 321:406).

Scientists define tachycardia and ventricular fibrillation as being of multiple nature. It now seems clear, and is accepted in the art, that re-entry is the underlying mechanism to most sustained arrhythmias. Prolonging ventricular repolarization as a means of preventing ventricular arrhythmias has consequently received renewed attention. This points to Class-III agents as drugs of choice in the treatment of arrhythmias. A Class-III agent, as referred to herein, is an agent which is classified as such in the Vaughan-Williams classification of anti-arrhythmic drugs. A Class-III agent exerts its primary anti-arrhythmic activity by prolonging cardiac action potential duration (APD), and thereby the effective refractory period (ERP), with no effect on conduction. These electrophysiological changes, which are brought about by blockade of cardiac potassium channels, are well known in the art, Because the blockade of cardiac potassium channels is not associated with depression of the contractile function of the heart, Class-III agents are particularly attractive for use in patients with CHF. Unfortunately, the existing Class-III agents are limited in their utility by additional pharmacological activities, lack of good oral bioavailability, or a poor toxicity profile The only two Class III agents currently marketed are bretylium (i.v. only) and amiodarone (i.v. and pro.).

Amiodarone is an anti-arrhythmic agent having vasodilator properties that may benefit patients with severe heart failure. Amiodarone has been shown to improve survival of post-myocardial infarction patients with asymptomatic high-grade ventricular arrhythmias, and it proved efficacious in patients resistant to other anti-arrhythmic drugs without impairing left ventricular function. Cardioprotective agents and methods which employ amiodarone in synergistic combination with vasodilators and beta blockers have been described for use in patients with coronary insufficiency (U.S. Pat. No. 5,175,187). Amiodarone has also been described for reducing arrhythmias associated with CHF as used in combination with antihypertensive agents, egg, (S)-1-[6-amino-2-[[hydroxy(4-phenylbutyl)phosphinyl] oxyl]-L-proline (U.S. Pat. No. 4,962,095) and zofenopril (U.S. Pat. No. 4,931,464). However, amiodarone is a difficult drug to manage because of its numerous side effects, some of which are serious.

The most serious long-term toxicity of amiodarone derives from its kinetics of distribution and elimination. It is absorbed slowly, with a low bioavailability and relatively long half-life. These characteristics have clinically important consequences, including the necessity of giving loading doses, a delay in the achievement of full anti-arrhythmic effects, and a protracted period of elimination of the drug after its administration has been discontinued.

Amiodarone also can interact negatively with numerous drugs including aprindine, digoxin, flecainide, phenytoin, procainamide, quinidine, and warfarin. It also has pharmacodynamic interactions with catecholamines, diltiazem, propranolol, and quinidine, resulting in alpha- and beta-antagonism, sinus arrest and hypotension, bradycardia and sinus arrest, and torsades de pointes and ventricular tachycardias, respectively. There is also evidence that amiodarone depresses vitamin K-dependent clotting factors, thereby enhancing the anticoagulant effect of warfarin.

Numerous adverse effects limit the clinical applicability of amiodarone. Important side effects can occur including corneal microdeposits, hyperthyroidism, hypothyroidism, hepatic dysfunction, pulmonary alveolitis, photosensitivity, dermatitis, bluish discoloration, and peripheral neuropathy.

Compounds of structural formula I:

and pharmaceutically acceptable salts thereof, wherein m is 0 to 4, n is 0 or 1, $X_1$ and $X_2$ are H, lower alkyl, or halogen, preferably iodine, $R_1$ and $R_2$ are lower alkyl, and $R_3$ is optionally substituted alkyl, heteroalkyl, cycloalkyl, heterocycloalkyl, aryl, heteroaryl. Preferably $R_3$ is (R)-2-butyl, (S)-2-butyl, (R)-3-methyl-2-butyl, or (S)-3-methyl-2-butyl.

The preferred compounds have the following formulas

1

2

3

-continued

4 and include pharmaceutically acceptable salts thereof, Particularly preferred salts are citrate, (L)-tartrate, (D)-tartrate, fumarate, maleate. These compounds are useful for treating mammals, including humans, suffering from ventricular and supraventricular arrhythmias, including atrial fibrillation.

These compounds, when administered to a mammal, including a human, give rise to metabolites that are useful for drug monitoring and that have electrophysiological properties of their own.

There is no Class-III agent presently marketed that can be used safely in patients with CHF. The cardiovascular drug market is the largest in any field of drug research, and an effective and safe Class-III anti-arrhythmic agent useful in patients with CHF is expected to be of substantial benefit. Therefore, a drug which could successfully improve the prognosis of CHF patients, but with a safety profile much improved over that of amiodarone, would be extremely useful and desired. Various analogs of amiodarone have been previously described (U.S. Pat. Nos. 6,710,070; 6,683,195; 6,372,783; 6,362,223; 6,316,487; 6,130,240; 5,849,788; 5,440,054; and 5,364,880). The subject invention adds to this arsenal of compounds,

SUMMARY OF THE INVENTION

The present invention provides compounds that have particular utility for treating life-threatening ventricular tachyarrhythmias, especially in patients with congestive heart failure (CHF).

The compounds of the subject invention also provide effective management for ventricular arrhythmias and supraventricular arrhythmias, including atrial fibrillation and re-entrant tachyarrhythmias involving accessory pathways.

More specifically, the novel compounds have the particular advantage of reducing the numerous side effects observed with the drugs currently available for treatment of these cardiac arrhythmias. For example, the compound of choice currently used for treating cardiac arrhythmias is amiodarone, which has side effects that can be serious. Because compounds of the invention are metabolites of compounds such as 1 to 4, they can be used for therapeutic drug monitoring in patients receiving therapeutic doses of compounds 1 to 4. An example is given in scheme 1 below where the metabolism of compound 1 is shown.

Scheme 1

Scheme 1 depicts the metabolism of compound 1 in animals, including humans. "A" denotes an ester cleavage metabolic reaction, and "B" denotes a N-dealkylation reaction, Scheme 1 shows that the parent drug, i.e., compound 1, can either undergo an ester cleavage metabolic reaction to compound 5, or can undergo a N-desethylation reaction to compound 6, which itself can undergo ester cleavage to compound 7, or N-desethylation to compound 8, which in turn can be cleaved by esterases to compound 9. Scheme 1 is given as an illustrative example. However, the metabolic scheme for compounds 2, 3, and 4 is similar to the scheme for compound 1.

DETAILED DISCLOSURE OF THE INVENTION

The subject invention provides novel compounds that can produce the desired pharmacological properties of amiodarone, but do not have the undesirable physiological properties of amiodarone, Specifically, long-term toxicity symptoms (pulmonary fibrosis, corneal microdeposits, etc) are reduced with the compounds of the subject invention In addition, the novel compounds are metabolites of compounds of structural formula 1, such as compounds 1 to 4 when compounds 1 to 4 are administered to a mammal, including a human These compounds can therefore be used to monitor drug levels and drug pharmacokinetics in patients receiving compounds 1 to 4.

The present invention provides substantially pure compounds of structural formula II:

II and pharmaceutically acceptable salts thereof, wherein $R_1$ is H or $C_1$-$C_{10}$ alkyl;

$R_2$ is H or optionally substituted $C_1$-$C_{10}$ alkyl, heteroalkyl, cycloalkyl, or heterocycloalkyl;

n=0 to 4;

p=0 or 1;

$R_3$ and $R_4$ are, independently, H or $C_1$-$C_4$ alkyl,

By "substantially pure" is meant that the compounds contain less than 20%, preferably less than 10%, and more preferably less than 5% impurities on a weight basis. ("Impurities" does not encompass pharmaceutically acceptable carriers, diluents, excipients, or the like.)

In particularly preferred embodiments, $R_1$ is ethyl; $R_2$ is (S)-2-butyl, (R)-2-butyl, (3)-3-methyl-2-butyl, or (R)-3-methyl-2-butyl; n=0 or 1, most preferably n=1; p=0; and, $R_3$ and $R_4$ are, independently, H or methyl Specifically exemplified herein are the following compounds (Compound 6 through Compound 9):

Compound 6

Compound 7

Compound 8

Compound 9

Particularly preferred compounds include (S)-{3-[4-(2-Ethylamino-ethoxy)-3,5-diiodo-benzoyl]-benzofuran-2-yl}-acetic acid sec-butyl ester; {3-[4-(2-Ethylamino-ethoxy)-3,5-diiodo-benzoyl]-benzofuran-2-yl)-acetic acid; (S)-(3-[4-(2-Amino-ethoxy)-3,5-diiodo-benzoyl]-benzofuran-2-yl}-acetic acid sec-butyl ester; {3-[4-(2-Amino-ethoxy)-3,5-diiodo-benzoyl]-benzofuran-2-yl}-acetic acid; (R)-{3-[4-(2-Ethylamino-ethoxy)-3,5-diiodo-benzoyl]-benzofuran-2-yl}-acetic acid sec-butyl ester; (R)-{3-[4-(2-Amino-ethoxy)-3,5-diiodo-benzoyl]-benzofuran-2-yl}-acetic acid sec-butyl ester; (5)-{3-[4-(2-Ethylamino-ethoxy)-3,5-diiodo-benzoyl]-benzofuran-2-yl}-acetic acid 1,2-dimethyl-propyl ester; (R)-(3-[4-(2-Ethylamino-ethoxy)-3,5-diiodo-benzoyl]-benzofuran-2-yl)-acetic acid 1,2-dimethyl-propyl ester; (S)-{3-[4-(2-Amino-ethoxy)-3,5-diiodo-benzoyl]- benzofuran-2-yl}-acetic acid 1,2-dimethyl-propyl ester; (R)-{3-[4-(2-Amino-ethoxy)-3,5-diiodo-benzoyl]-benzofuran-2-yl}-acetic acid 1,2-dimethyl-propyl ester.

The novel compounds can also be provided in their salt form. Thus, the invention includes pharmaceutically acceptable salts, for example acid addition salts derived from inorganic or organic acids, such as hydrochlorides, hydrobromides, p-toluenesulfonates, phosphates, sulfates, perchlorates, acetates, trifluororacetates, proprionates, citrates, malonates, succinates, lactates, oxalates, (L)-tartrates, (D)-tartrates, meso-tartrates, and benzoates. Salts may also be derived from bases (organic and inorganic), such as alkali metal salts (e.g., magnesium or calcium salts), or organic amine salts, such as morpholine, piperidine, dimethylamine, or diethylamine salts.

The compounds of the subject invention can be readily made by a person skilled in the art having the benefit of the current disclosure and, for example, the disclosures in U.S. Pat. Nos. 6,710,070; 6,683,195; 6,372,783; 6,362,223; 6,316,487; 6,130,240; 5,849,788; 5,440,054; and 5,364,880. These patents are incorporated herein by reference Additional modifications of the compounds disclosed herein can readily be made by those skilled in the art. Thus, analogs and salts of the exemplified compounds are within the scope of the subject invention. With knowledge of the compounds of the subject invention skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound Analogs of the exemplified compounds can be readily prepared using commonly known, standard reactions. These standard reactions include, but are not limited to, hydrogenation, methylation, acetylation, halogenation, and acidification reactions. For example, new salts within the scope of the invention can be made by adding mineral acids, e.g., HCl H$_2$SO$_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention, The subject invention further pertains to enantiomerically isolated compounds, and compositions comprising the compounds, for calcium channel blocking. The isolated enantiomeric forms of the compounds of the invention are substantially free from one another (i.e., in enantiomeric excess), In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess A further aspect of the subject invention pertains to the breakdown products which are produced when the therapeutic compounds of the subject invention are acted upon by hydrolytic enzymes, such as esterases. The presence of these breakdown products in urine or serum can be used to monitor the rate of clearance of the therapeutic compound from a patient The successful application of the new compounds to the treatment of CHF is evidenced by the evaluation of the thermodynamic properties of the compound, e.g., measuring its partition coefficient between water and octanol, evaluation of its kinetics of elimination by measuring its stability in buffer and in human plasma, and evaluation of its electrophysiological properties in guinea pig heart preparations.

More specifically, the novel compounds can be used for treating life-threatening ventricular tachyarrhythmias, especially in patients with congestive heart failure. Thus, the compounds of the subject invention provide effective management of not only ventricular tachyarrhythmias and less severe ventricular arrhythmias, but also atrial fibrillation and re-entrant tachyarrhythmias involving accessory pathways, A composition comprising a novel compound having a rapid elimination rate can offer many advantages over the currently available anti-arrhythmic agents such as amiodarone, These advantages include:
(i) a shorter onset of action,
(ii) decreased and more manageable long-term toxicity, and
(iii) lower potential for drug-drug interactions In addition, the novel compounds can be included in a composition comprising a second active ingredient. The second active ingredient can be useful for concurrent or synergistic treatment of arrhythmia or for the treatment of an unrelated condition which can be present with or result from arrhythmia or CHF.

The subject compounds have thermodynamic properties similar to those of amiodarone, but provide the advantageous property of being rapidly metabolized in plasma to a water-soluble metabolite. More specifically, the subject compounds are Class-III agents with electronic, steric, and thermodynamic properties comparable to those of amiodarone, but with an enzymatically labile ester group advantageously built into the structure such that the drug can be readily hydrolyzed in plasma to a polar, water-soluble metabolite. This water-soluble metabolite can be eliminated by the kidneys. This is a definite advantage over amiodarone, which is metabolized primarily in the liver, Under such conditions, the elimination of the novel compounds are increased and results in a more rapid dissociation of the drug from phospholipid-binding sites. The accumulation of the compound, which is dependent on the steady-state tissue concentration of the drug, and therefore on the dose, then becomes easily reversible. It follows that, upon discontinuation of a drug comprising one of the novel compounds, clearance from the body is more rapid. This increased elimination makes anti-arrhythmic therapy using the subject compounds or compositions comprising the subject compounds easier to manage.

Furthermore, the compounds of the invention may be administered in conjunction with other compounds, or compositions thereof. These compounds, and compositions thereof, may include additional compounds known to be useful for the treatment of cardiac arrhythmias, cardioprotective agents, antibiotics, antiviral agents, or thrombolytic agents (e.g., streptokinase, tissue plasminogen activator, or recombinant tissue plasminogen activator). The compounds and compositions of the invention can have particular usefulness for treating life-threatening ventricular tachyarrhythmias, especially in patients with congestive heart failure (CHF), Post-myocardial infarction patients can also benefit from the administration of the subject compounds and compositions; thus, methods of treating post-myocardial infarction patients are also provided by the subject invention An "individual" or "patient" includes animals and humans in need of treatment for arrhythmias. In a preferred embodiment, the individual is a human.

Cardioprotective agents include vasodilators and beta blockers described for use in patients with coronary insufficiency (such as those of U.S. Pat. No. 5,175,187 or others known to the skilled artisan). Other cardioprotective agents include known anti-hypertensive agents, e.g., (S)-1-[6-amino-2-[[hydroxy(4-phenylbutyl)phosphinyl]oxyl]-L-proline (U.S. Pat. No. 4,962,095) and zofenopril (U.S. Pat. No. 4,931,464). Additional cardioprotective agents include, but are not limited to, aspirin, heparin, warfarin, digitalis, digitoxin, nitroglycerin, isosorbide dinitrate, hydralazine, nitroprusside, captopril, enalapril, and lisinopril.

The compounds and compositions also provide effective management for ventricular arrhythmias and supraventricular arrhythmias, including atrial fibrillation and reentrant tachyarrhythmias involving accessory pathways. Compounds and compositions of the invention are also useful for the treatment of ventricular and supra-ventricular arrhythmias, including atrial fibrillation and flutter, paroxysmal supraventricular tachycardia, ventricular premature beats (VPB), sustained and non-sustained ventricular tachycardia (WV), and ventricular fibrillation (VF), Other non-limiting examples of the arrhythmias which may be treated by the compounds of the instant invention include: narrow QRS tachycardia (atrial, intra-/para-A-V node, or accessory pathway), ventricular tachycardia, and ventricular arrhythmias in cardiomyopathy.

The compounds of this invention have therapeutic properties similar to those of the unmodified parent compounds Accordingly, dosage rates and routes of administration of the disclosed compounds are similar to those already used in the art and known to the skilled artisan, (See, for example, *Physicians' Desk Reference*, 54$^{th}$ Ed., Medical Economics Company, Montvale, N.J., 2000.)

The compounds of the subject invention can be formulated according to known methods for preparing pharmaceutically useful compositions. Formulations are described in detail in a number of sources which are well known and readily available to those skilled in the art, For example, *Remington's Pharmaceutical Science* by E. W. Martin describes formulation which can be used in connection with the subject invention. In general, the compositions of the subject invention are formulated such that an effective amount of the bioactive compound(s) is combined with a suitable carrier in order to facilitate effective administration of the composition, In accordance with the subject invention, pharmaceutical compositions are provided which comprise, as an active ingredient, an effective amount of one or more of the compounds and one or more non-toxic, pharmaceutically acceptable carriers or diluents, Examples of such carriers for use in the invention include ethanol, dimethyl sulfoxide, glycerol, silica, alumina, starch, and equivalent carriers and diluents, Further, acceptable carriers can be either solid or liquid. Solid form preparations include powders, tablets, pills, capsules, cachets, suppositories and dispersible granules. A solid carrier can be one or more substances that may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenges.

For purposes of the present invention, the following definitions will be used (unless expressly stated otherwise):

For simplicity, chemical moieties are defined and referred to throughout primarily as univalent chemical moieties (e.g., alkyl, aryl, etc.), Nevertheless, such terms are also used to convey corresponding multivalent moieties under the appropriate structural circumstances clear to those skilled in the art. For example, while an "alkyl" moiety generally refers to a monovalent radical (erg. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for 0, and 2, 4, or 6 for S, depending on the oxidation state of the S). On occasion a moiety may be defined, for example, as $(A)_a$-B—, wherein a is 0 or 1. In such instances, when a is 0 the moiety is B– and when a is 1 the moiety is A-B—.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents, Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$alkyl") is a covalent bond (like "$C_0$" hydrocarbyl). As used herein "lower alkyl" means an alkyl moiety of 1 to 6 carbons.

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents, Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene, The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N, An "aryl" group is a $C_6$-$C_{14}$ aromatic moiety comprising one to three aromatic rings, which is optionally substituted Preferably, the aryl group is a $C_6$-$C_{10}$ aryl group. Preferred aryl groups include, without limitation, phenyl, naphthyl, anthracenyl, and fluorenyl An "aralkyl" or "aralkyl" group comprises an aryl group covalently linked to an alkyl group, either of which may independently be optionally substituted or unsubstituted Preferably, the aralkyl group is ($C_1$-$C_6$)alk ($C_6$-$C_{10}$)aryl, including, without limitation, benzyl, phenethyl, and naphthylmethyl.

A "heterocyclic" group (alternatively referred to as "heterocyclyl" or "heterocycloalkyl") is an optionally substituted non-aromatic mono-, bi-, or tricyclic structure having from about 3 to about 14 atoms, wherein one or more atoms are selected from the group consisting of N, O, and S. One ring of a bicyclic heterocycle or two rings of a tricyclic heterocycle may be aromatic, as in indan and 9,10-dihydroanthracene. The heterocyclic group is optionally substituted on carbon with oxo or with one of the substituents listed above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

As used herein, the term "heteroaryl" refers to optionally substituted groups having 5 to 14 ring atoms, preferably 5, 6, 9, or 10 ring atoms; having 6, 10, or 14 pi electrons shared in a cyclic array; and having, in addition to carbon atoms, between one or more heteroatoms selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, triazolyl, and isoxazolyl.

A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$-$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH-substituted with oxo is —C(O)—) nitro, halohydrocarbyl, hydrocarbyl, aryl, aralkyl, alkoxy, haloalkoxy, aryloxy, heteroaryloxy, amino, acylamino, alkylcarbamoyl, arylcarbamoyl, aminoalkyl, acyl, carboxy, hydroxyalkyl, alkanesulfonyl, arenesulfonyl, sulfonamido, alkanesulfonamido, arenesulfonamido, aralkylsulfonamido, alkylcarbonyl, acyloxy, cyano, alkylthio, ureido, and ureidoalkyl groups. Preferred substituents, which are themselves not further substituted (unless expressly stated otherwise) are:

(a) halo, cyano, oxo, alkyl, alkoxy, alkylthio, haloalkoxy, aminoalkyl, aminoalkoxy, carboxy, formyl, nitro, amino, amidino, carbamoyl, guanidino, $C_3$-$C_7$ heterocycle, heterocyclylalkyl, heterocyclylcarbonyl, hydroxyalkyl, alkoxyalkyl, (b) $C_1$-$C_5$ alkyl or alkenyl or arylalkyl imino, carbamoyl, carbamate, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, heteroarylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, heteroaryloxy, arylalkyl ether, $C_3$-$C_7$ heterocyclylalkylether, aryl, aryl fused to a cycloalkyl or heterocycle or another aryl ring, $C_3$-$C_7$ heterocyclyl, heteroaryl, arylcarbamoyl, or any of these rings fused or spiro-fused to a cycloalkyl, heterocyclyl, or aryl, wherein any of the foregoing which are additionally substitutable is further optionally substituted with one more moieties listed in (a), above; and (c) —$(C_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$-$C_3$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

In addition, substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tricyclic fused ring system. For example, an optionally substituted phenyl includes, but not limited to, the following:

Preferred substituents on cyclic moieties (i.e., cycloalkyl, heterocyclyl, aryl, heteroaryl) also include groups of the formula —$K^1$—$N(H)(R^{10})$, wherein $K^1$ is a $C_0$-$C_4$ alkylene;

$R^{10}$ is $C_1$-$C_4$ alkylene -$Z'$, and $Z'$ is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings A "halohydrocarbyl" is a hydrocarbyl moiety in which from one to all hydrogens have been replaced with one or more halo.

The term "halogen" or "halo" as employed herein refers to chlorine, bromine, fluorine, or iodine, As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

Throughout the specification preferred embodiments of one or more chemical substituents are identified. Also preferred are combinations of preferred embodiments, Some compounds of the invention may have chiral centers and/or geometric isomeric centers (E- and Z-isomers), and it is to be understood that the invention encompasses all such optical, diastereoisomers and geometric isomers. The invention also comprises all tautomeric forms of the compounds disclosed herein. Where compounds of the invention include chiral centers, the invention encompasses the enantiomerically pure isomers of such compounds, the enantiomerically enriched mixtures of such compounds, and the racemic mixtures of such compounds, Following are examples that illustrate aspects of the subject invention. These examples should not be construed as limiting,

EXAMPLE 1

Electrophysiological Effects of Compound 6

The model used to test the electrophysiological properties of Compound 6 utilized atrial-paced (cycle length=300 ms) guinea pig isolated hearts perfused with Krebs-Henseleit solution at 36° C. The following recordings were made:

Electrophysiological Recordings: atrial and His-bundle electrograms.

EP Measurements: SA, AH, HV, QRS and QT intervals.

Figure 1:
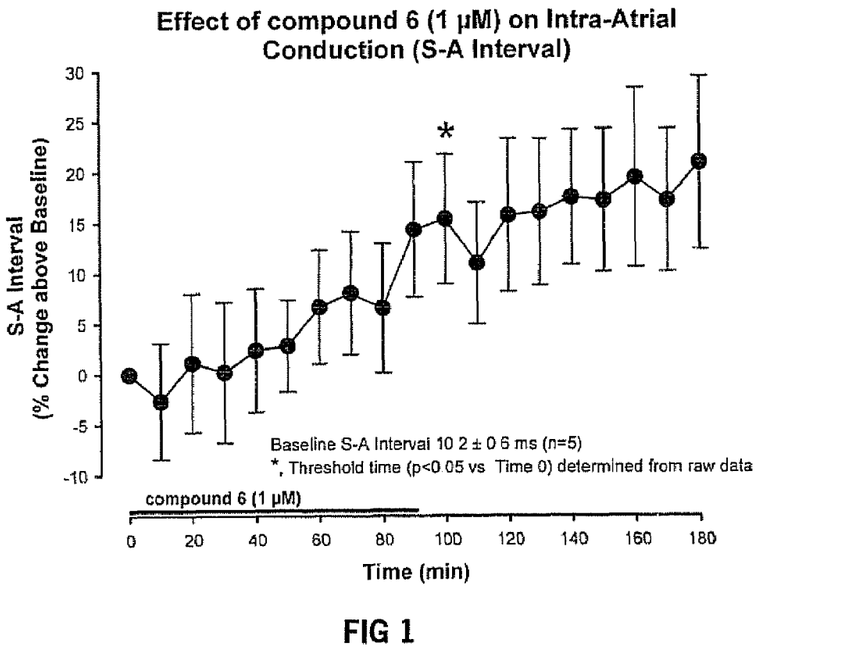
FIG. 1 shows the time course of effect of Compound 6 (1 µM) on Intra-Atrial Conduction (S-A Interval).
Figure 2:
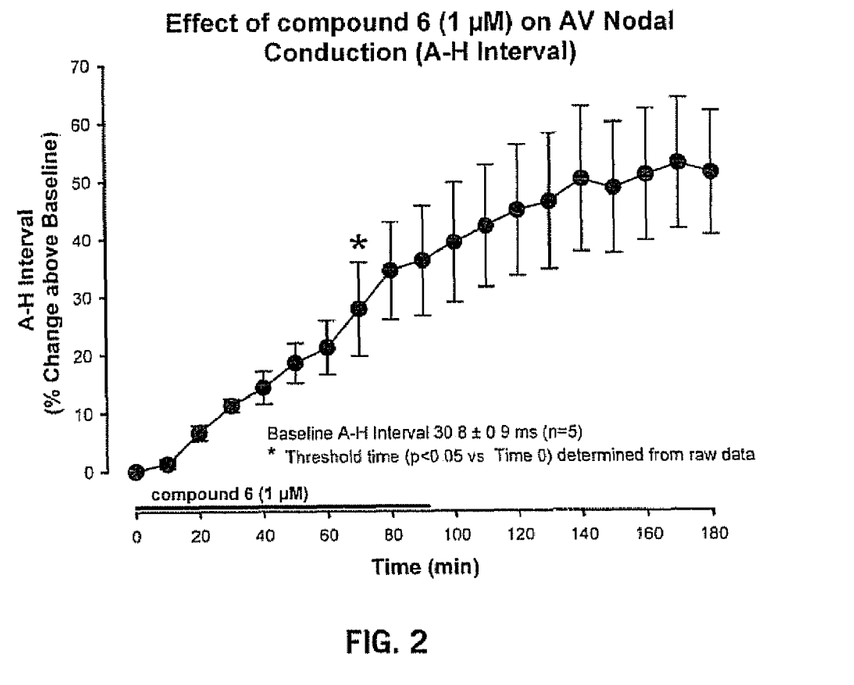
FIG. 2 shows the Time Course of Effect of Compound 6 (1 µM) on AV Nodal Conduction (A-H Interval).
Figure 3:
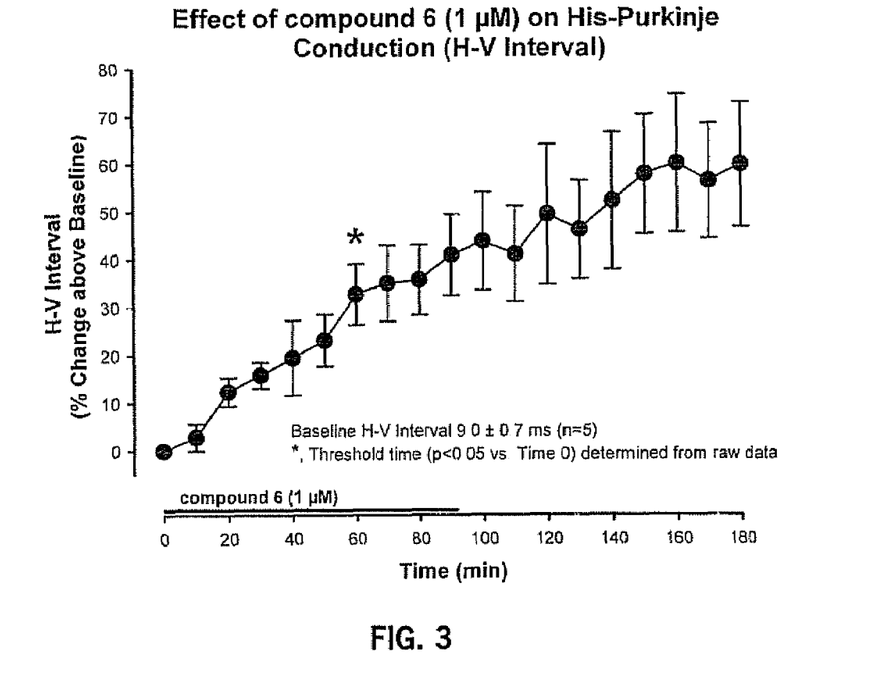
FIG. 3 shows the Time Course of Effect of Compound 6 (1 µM) on His-Purkinje Conduction (H-V Interval)
Figure 4:
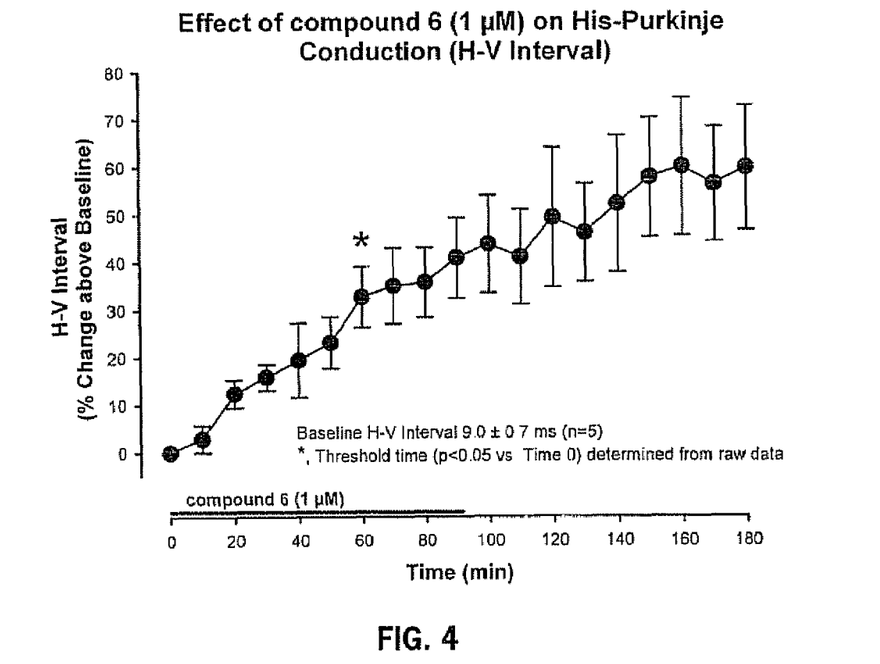
FIG. 4 shows the Time Course of Effect of Compound 6 (1 µM) on Intra-ventricular Conduction (QRS Interval).
Figure 5:
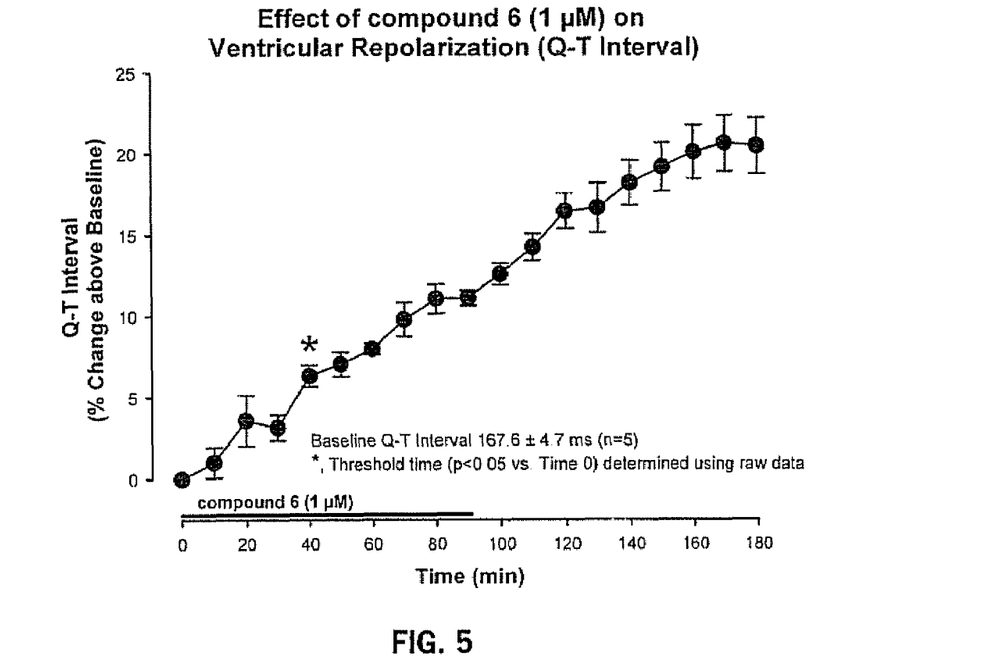
FIG. 5 shows the Time Course of Effect of Compound 6 (1 μM) on Ventricular Repolarization (Q-T Interval)
Figure 6:
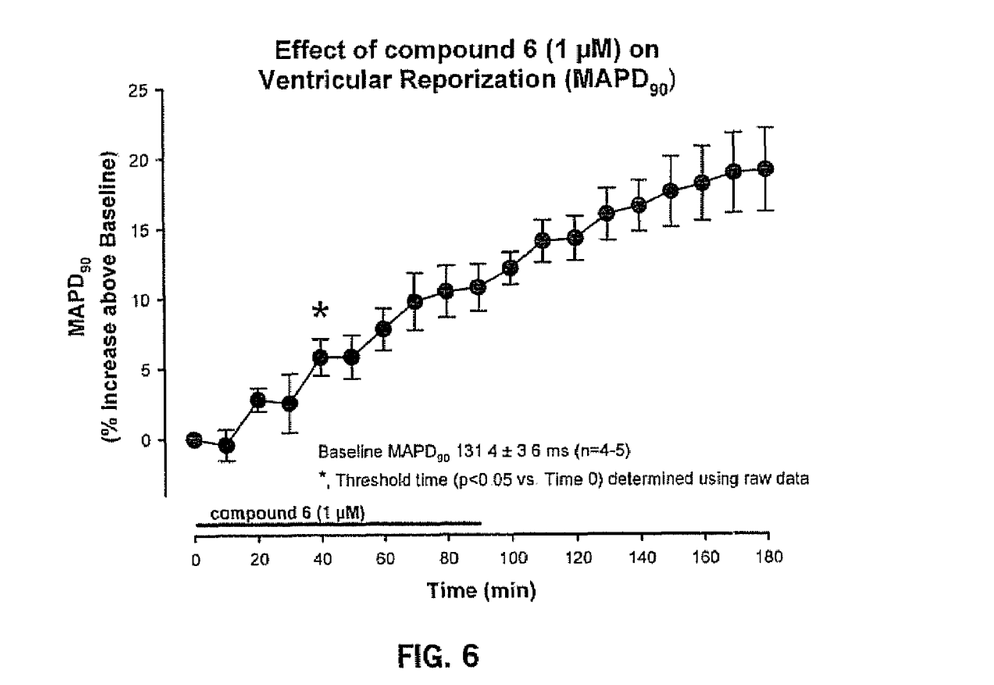
FIG. 6 shows the Time Course of Effect of Compound 6 (1 μM) on Ventricular Repolarization (MAPD$_{90}$).

Compound 6 was given via infusion pump into perfusate line, Time-dependent EP effects were measured at 1 μM Compound 6. Compound 6 was infused for 90 minutes, then washed for 90 minutes. EP measurements were made Q 10 minutes. Data was analyzed by 1 way repeated measures ANOVA followed by SNK testing for multiple comparisons, The results are presented in FIGS. 1-6.

EXAMPLE 2

Electrophysiological Effects of Compound 7

The model used to test the electrophysiological properties of Compound 7 utilized atrial-paced (cycle length=300 ms) guinea pig isolated hearts perfused with Krebs-Henseleit solution at 36° C., The following recordings were made:

Electrophysiological Recordings, atrial and His-bundle electrograms.

EP Measurements. SA, AH, HV, QRS and QT intervals.

Figure 7:
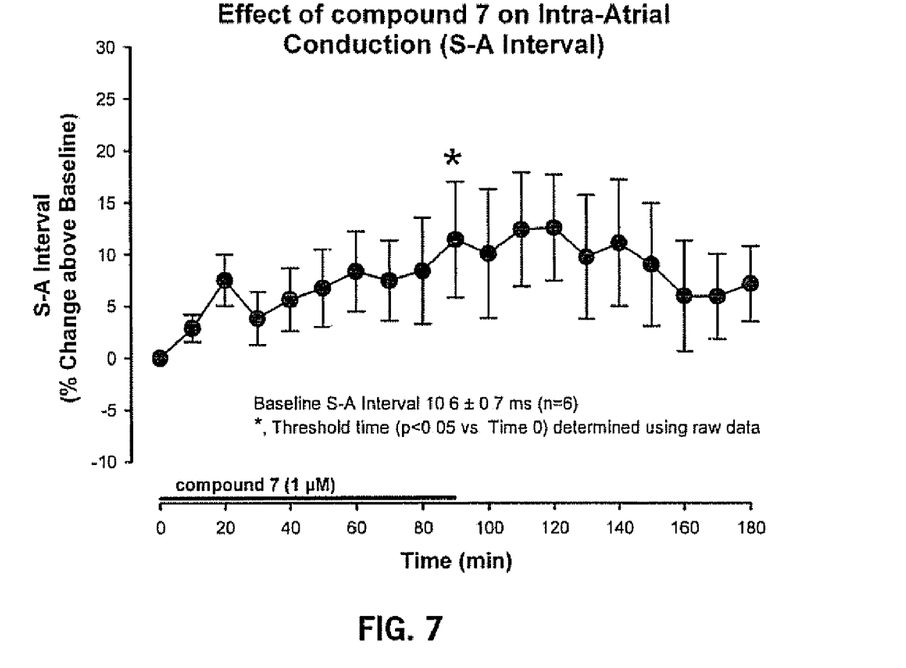
FIG. 7 shows the Time Course of Effect of Compound 7 (1 μM) on Intra-Atrial Conduction (S-A Interval).
Figure 8:
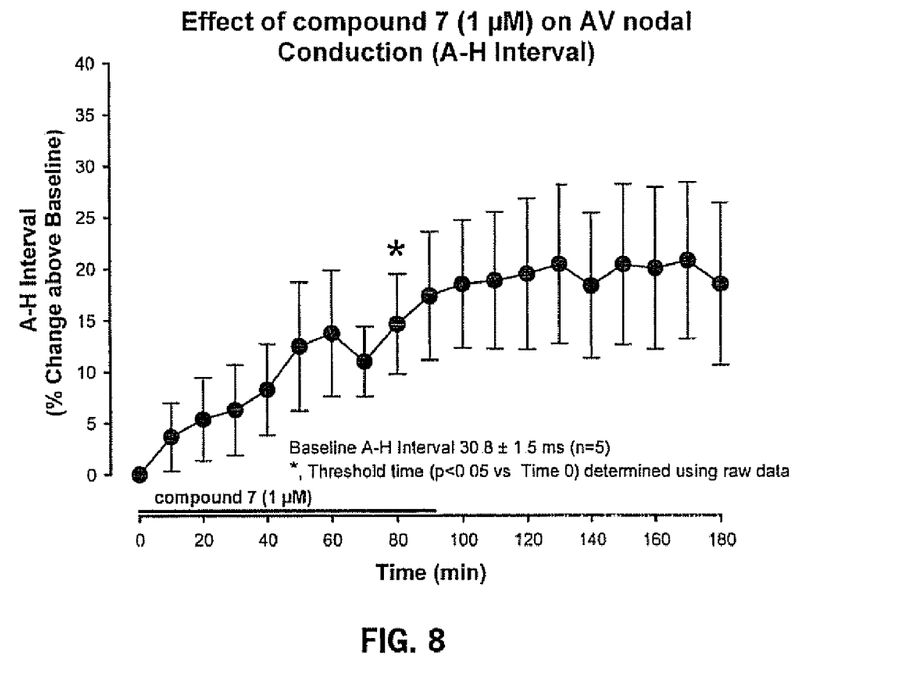
FIG. 8 shows the Time Course of Effect of Compound 7 (1 μM) on AV nodal Conduction (A-H Interval).
Figure 9:
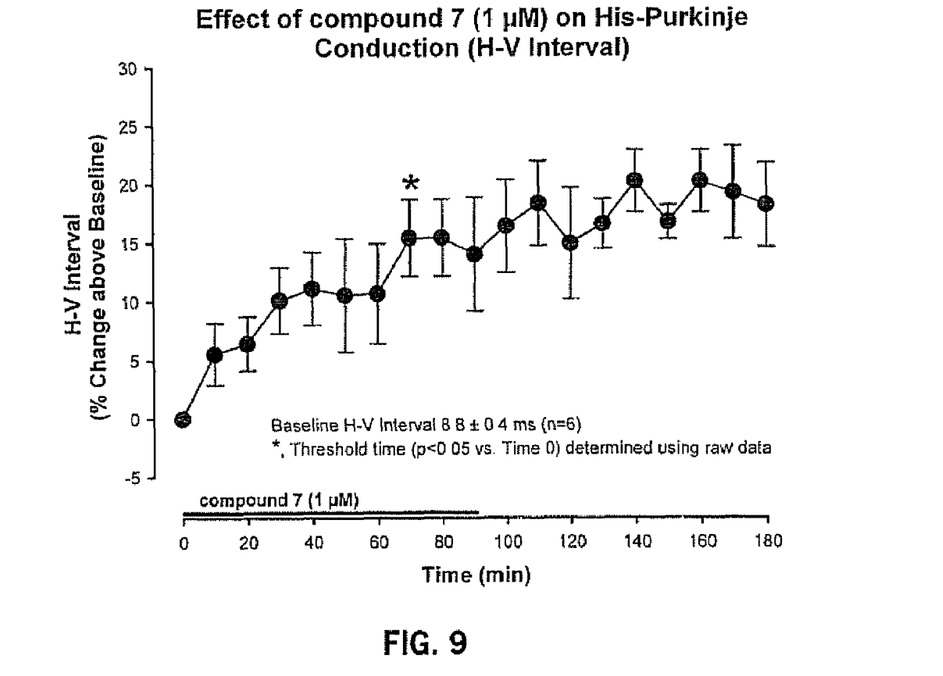
FIG. 9 shows the Time Course of Effect of Compound 7 (1 μM) on His-Purkinje Conduction (H-V Interval)
Figure 10:
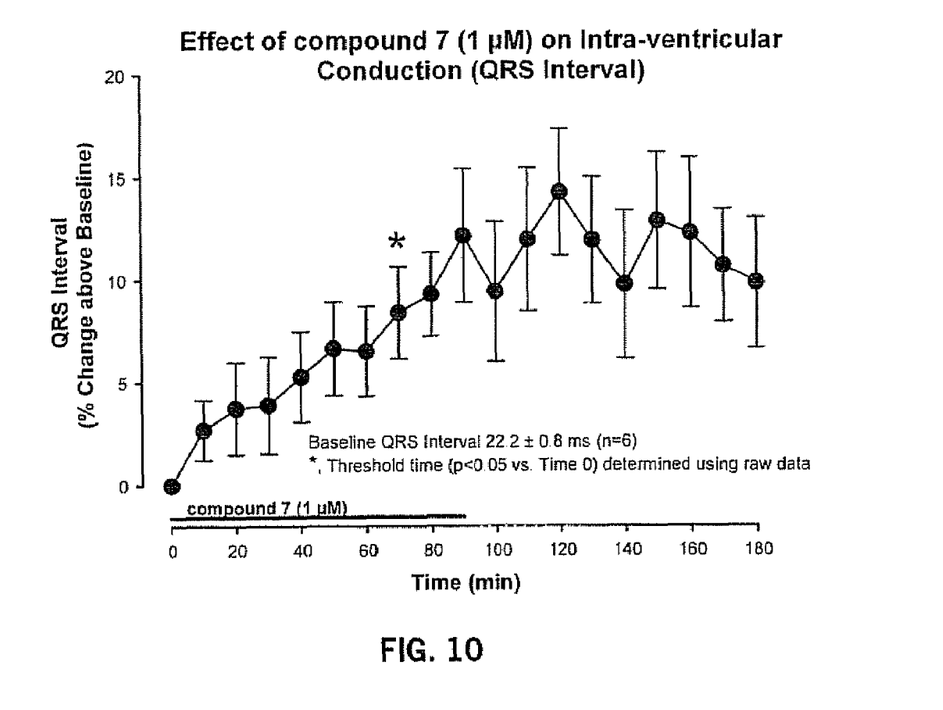
FIG. 10 shows the Time Course of Effect of Compound 7 (1 μM) on Intral-ventricular Conduction (QRS Interval)
Figure 11:
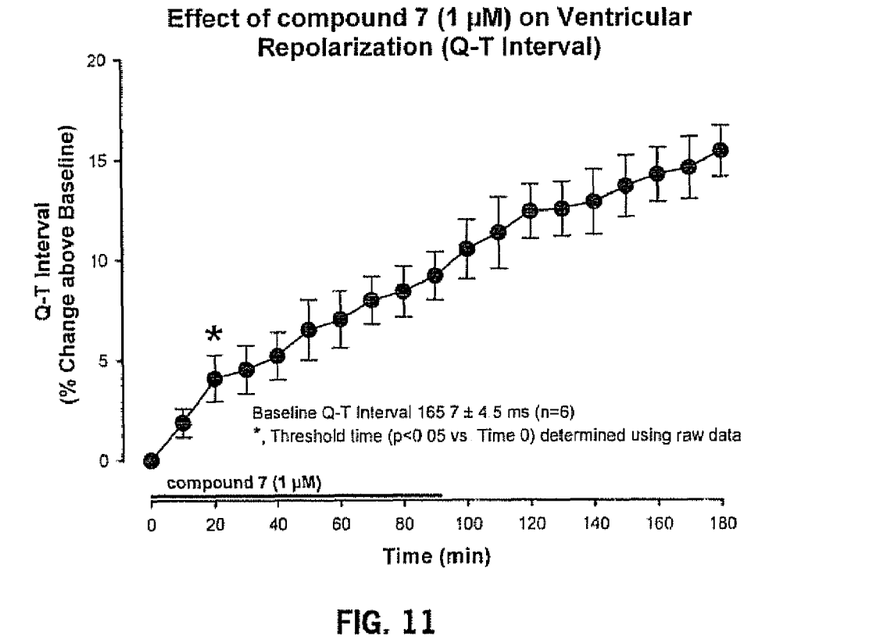
FIG. 11 shows the Time Course of Effect of Compound 7 (1 μM) on Ventricular Repolarization (Q-T Interval)
Figure 12:
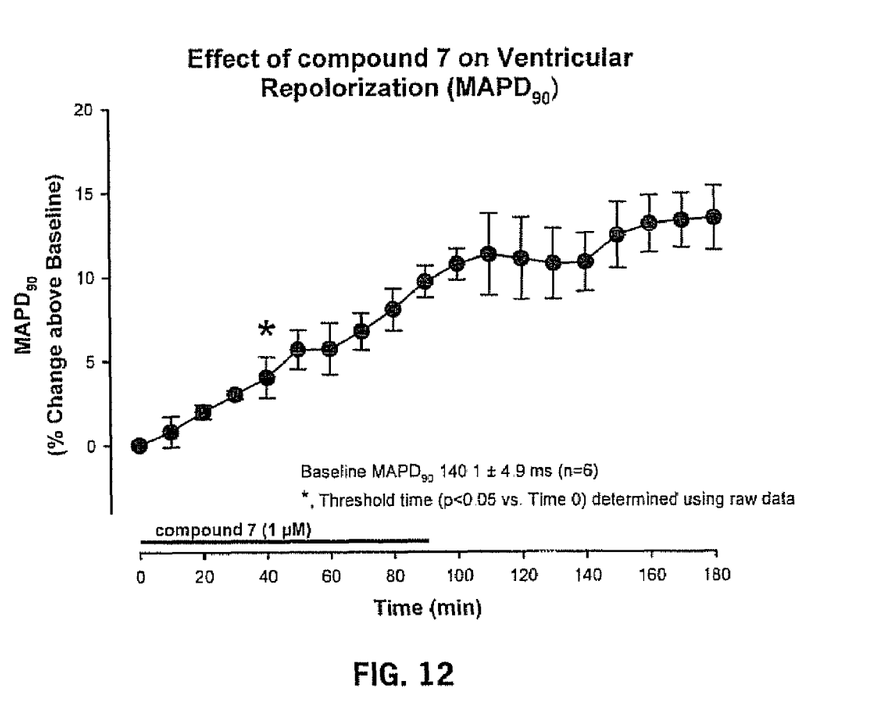
FIG. 12 shows the Time Course of Effect of Compound 7 (1 μM) on Ventricular Repolorization (MAPD$_{90}$)

Compound 7 was given via infusion pump into perfusate line. Time-dependent EP effects were measured at 1 μM Compound 7. Compound 7 was infused for 90 minutes, then washed for 90 minutes. EP measurements were made Q 10 minutes Data was analyzed by 1 way repeated measures ANOVA followed by SNK testing for multiple comparisons The results are presented in FIGS. 7-12,

EXAMPLE 3

Synthesis of Compounds

The compounds of the subject invention can be readily made, or isolated, by a person skilled in the art having the benefit of the current disclosure as well as, for example, the disclosures in U.S. Pat. Nos. 6,710,070; 6,683,195; 6,372,783; 6,362,223; 6,316,487; 6,130,240; 5,849,788; 5,440,054; and 5,364,880, Schemes 2 and 3 provide synthesis procedures for making compounds 6 and 7 (examples where the ester moiety is (S)-2-butyl)

Specific reaction conditions can be readily determined by chemists skilled in the art having the current disclosure In addition, a reasonably skilled chemist will recognize that the same synthetic scheme can be applied to make the compounds of the subject invention, Scheme 2: (a) benzyl bromde/triethylamine (b) Tosyl chloride/triethylamine Scheme 3: (a) compound 12/$KHCO_3$/toluene/water (b) 1-chloroethyl chloroformate/methanol (c) $H_2SO_4$ All patents, patent applications, provisional applications, and publications referred to or are incorporated by reference in their entirety, including all figures and tables, to the are not inconsistent with the explicit teachings of this specification. It should be understood that the examples and embodiments described herein are for purposes only and that various modifications or changes in light thereof will be suggested skilled in the art and are to be included within the spirit and purview of this application.

We claim:

1. A pharmaceutically acceptable salt of a compound of structural Formula II:

II wherein
$R_1$ is H or $C_1$-$C_{10}$ alkyl;
$R_2$ is H or optionally substituted $C_1$-$C_{10}$ alkyl, heteroalkyl, cycloalkyl or heterocycloalkyl;
n=0 to 4;
p=0 or 1;
$R_3$ and $R_4$ are, independently, H or $C_1$-$C_4$ alkyl, and wherein the salt is selected from hydrochloride, hydrobromide, p-toluenesulfonate, phosphate, sulfate, perchlorate, acetate, trifluororacetate, propionate, citrate, malonate, succinate, lactate, oxalate, (L)-tartrate, (D)- tartrate, meso-tartrate, benzoate, alkali metal, morpholine, piperidine, dimethylamine, and diethylamine salts.

2. The salt according to claim 1 wherein
R$_1$ is H or ethyl;
R$_2$ is (S)-2-butyl, (R)-2-butyl, (S)-3-methyl-2-butyl or (R)-3-methyl-2-butyl;
n=0 or 1;
p=0; and
R$_3$ and R$_4$ are, independently, H or methyl.

3. The salt according to claim 2 wherein R$_1$ is ethyl.

4. The salt according to claim 2 wherein n is 1.

5. The salt according to claim 2 wherein R$_1$ is ethyl and n is 1.

6. The salt according to claim 1 wherein the compound is selected from:

Compound 6

Compound 7

Compound 8

Compound 9

7. The salt according to claim 1 wherein the compound is selected from:
a) (S)-{3-[4-(2-Ethylamino-ethoxy)-3,5-diiodo-benzoyl]-benzofuran-2-yl}-acetic acid sec-butyl ester;
b) {3-[4-(2-Ethylamino-ethoxy)-3,5-diiodo-benzoyl]-benzofuran-2-yl}-acetic acid;
c) (S)-{3-[4-(2-Amino-ethoxy)-3,5-diiodo-benzoyl]-benzofuran-2-yl}-acetic acid sec-butyl ester;
d) {3-[4-(2-Amino-ethoxy)-3,5-diiodo-benzoyl]-benzofuran-2-yl}-acetic acid;
e) (R)-{3-[4-(2-Ethylamino-ethoxy)-3,5-diiodo-benzoyl]-benzofuran-2-yl}-acetic acid sec-butyl ester;
f) (R)-{3-[4-(2-Amino-ethoxy)-3,5-diiodo-benzoyl]benzofuran-2-yl}-acetic acid sec-butyl ester;
g) (S)-{3-[4-(2-Ethylamino-ethoxy)-3,5-diiodo-benzoyl]benzofuran-2-yl}-acetic acid 1,2-dimethyl-propyl ester;
h) (R)-{3-[4-(2-Ethylamino-ethoxy)-3,5-diiodo-benzoyl]-benzofuran-2-yl}-acetic acid 1,2-dimethyl-propyl ester;
i) (S)-{3-[4-(2-Amino-ethoxy)-3,5-diiodo-benzoyl]benzofuran-2-yl}-acetic acid 1,2-dimethyl-propyl ester; and
j) (R)-{3-[4-(2-Amino-ethoxy)-3,5-diiodobenzoyl]benzofuran-2-yl}-acetic acid 1,2-dimethyl-propyl ester.

8. A composition comprising a salt according to claim 1 and a pharmaceutically acceptable carrier, diluent, or excipient.

9. A composition comprising a salt according to claim 2 and a pharmaceutically acceptable carrier, diluent, or excipient.

10. A composition comprising a salt according to claim 3 and a pharmaceutically acceptable carrier, diluent, or excipient.

11. A composition comprising a salt according to claim 4 and a pharmaceutically acceptable carrier, diluent, or excipient.

12. A composition comprising a salt according to claim 5 and a pharmaceutically acceptable carrier, diluent, or excipient.

13. A composition comprising a salt according to claim 6 and a pharmaceutically acceptable carrier, diluent, or excipient.

14. A composition comprising a salt according to claim 7 and a pharmaceutically acceptable carrier, diluent, or excipient.

15. A compound of structural Formula II:

or a pharmaceutically acceptable salt thereof, wherein
R$_1$ is H or C$_1$-C$_{10}$ alkyl;
R$_2$ is H or optionally substituted C$_1$-C$_{10}$ alkyl, heteroalkyl, cycloalkyl or heterocycloalkyl;
n=0 to 4;

p=0 or 1;
R$_3$ and R$_4$ are, independently, H or C$_1$-C$_4$ alkyl;
and wherein a compound contains less than 20% impurities on a weight basis.

16. A compound according to claim 15 wherein a compound contains less than 10% impurities.

17. A compound according to claim 16 wherein a compound contains less than 5% impurities.

18. The compound according to claim 15 wherein
R$_1$ is H or ethyl;
R$_2$ is (S)-2-butyl, (R)-2-butyl, (S)-3-methyl-2-butyl or (R)-3-methyl-2-butyl;
n=0 or 1;
p=0; and
R$_3$ and R$_4$ are, independently, H or methyl.

19. A compound according to claim 18 wherein a compound contains less than 10% impurities.

20. A compound according to claim 19 wherein a compound contains less than 5% impurities.

21. The compound according to claim 18 wherein R$_1$ is ethyl.

22. A compound according to claim 21 wherein a compound contains less than 10% impurities.

23. A compound according to claim 22 wherein a compound contains less than 5% impurities.

24. The compound according to claim 18 wherein n is 1.

25. A compound according to claim 24 wherein a compound contains less than 10% impurities.

26. A compound according to claim 25 wherein a compound contains less than 5% impurities.

27. A compound according to claim 18 wherein R$_1$ is ethyl and n is 1.

28. A compound according to claim 27 wherein a compound contains less than 10% impurities.

29. A compound according to claim 28 wherein a compound contains less than 5% impurities.

30. The compound according to claim 15 wherein compound is selected from:

Compound 6

Compound 7

Compound 8

Compound 9

31. A compound according to claim 30 wherein a compound contains less than 10% impurities.

32. A compound according to claim 31 wherein a compound contains less than 5% impurities.

33. The compound according to claim 15 wherein the compound is selected from:
a) (S)-{3-[4-(2-Ethylamino-ethoxy)-3,5-diiodo-benzoyl]-benzofuran-2-yl}-acetic acid sec-butyl ester;
b) {3-[4-(2-Ethylamino-ethoxy)-3,5-diiodo-benzoyl]-benzofuran-2-yl}-acetic acid;
c) (S)-{3-[4-(2-Amino-ethoxy)-3,5-diiodo-benzoyl]-benzofuran-2-yl}1-acetic acid sec-butyl ester;
d) {3-[4-(2-Amino-ethoxy)-3,5-diiodo-benzoyl]-benzofuran-2-yl}-acetic acid;
e) (R)-{3-[4-(2-Ethylamino-ethoxy)-3,5-diiodo-benzoyl]-benzofuran-2-yl}-acetic acid sec-butyl ester;
f) (R)-{3-[4-(2-Amino-ethoxy)-3,5-diiodo-benzoyl]benzofuran-2-yl}-acetic acid sec-butyl ester;
g) (S)-{3-[4-(2-Ethylamino-ethoxy)-3,5-diiodo-benzoyl]benzofuran-2-yl}-acetic acid 1,2-dimethyl-propyl ester;
h) (R)-{3-[4-(2-Ethylamino-ethoxy)-3,5-diiodo-benzoyl]-benzofuran-2-yl}-acetic acid 1,2-dimethyl-propyl ester;
i) (S)-{(3-[4-(2-Amino-ethoxy)-3,5-diiodo-benzoyl]benzofuran-2-yl}-acetic acid 1,2-dimethyl-propyl ester; and
j) (R)-{3-[4-(2-Amino-ethoxy)-3,5-diiodobenzoyl]benzofuran-2-yl}-acetic acid 1,2-dimethyl-propyl ester.

34. A compound according to claim 33 wherein a compound contains less than 10% impurities.

35. A compound according to claim 34 wherein a compound contains less than 5% impurities.

36. A composition comprising a compound according to claim 16 and a pharmaceutically acceptable carrier, diluent, or excipient.

37. A composition comprising a compound according to claim 19 and a pharmaceutically acceptable carrier, diluent, or excipient.

38. A composition comprising a compound according to claim 22 and a pharmaceutically acceptable carrier, diluent, or excipient.

39. A composition comprising a compound according to claim 25 and a pharmaceutically acceptable carrier, diluent, or excipient.

40. A composition comprising a compound according to claim 28 and a pharmaceutically acceptable carrier, diluent, or excipient.

41. A composition comprising a compound according to claim 31 and a pharmaceutically acceptable carrier, diluent, or excipient.

42. A composition comprising a compound according to claim 34 and a pharmaceutically acceptable carrier, diluent, or excipient.

* * * * *